(12) United States Patent
Garcia-Garcia et al.

(10) Patent No.: US 9,913,800 B2
(45) Date of Patent: Mar. 13, 2018

(54) COMPOSITIONS AND METHODS FOR IMPROVING SKIN HEALTH

(71) Applicant: The Procter & Gamble Company, Cincinnati, OH (US)

(72) Inventors: Jose Carlos Garcia-Garcia, Cincinnati, OH (US); Jeffrey Alan Henry, Cincinnati, OH (US); Brian W. Howard, Liberty Township, OH (US); Nicholas William Geary, Mariemont, OH (US); Raul Victorino Nunes, Loveland, OH (US); Freddy Arthur Barnabas, West Chester, OH (US); Safa Motlagh, Dayton, OH (US); Yiping Sun, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/140,523

(22) Filed: Apr. 28, 2016

(65) Prior Publication Data

US 2016/0317432 A1    Nov. 3, 2016

Related U.S. Application Data

(60) Provisional application No. 62/153,557, filed on Apr. 28, 2015.

(51) Int. Cl.
*A61K 8/99*    (2017.01)
*C12N 1/20*    (2006.01)
(Continued)

(52) U.S. Cl.
CPC ............... *A61K 8/99* (2013.01); *A61K 35/74* (2013.01); *A61Q 19/00* (2013.01); *C12N 1/20* (2013.01);
(Continued)

(58) Field of Classification Search
CPC ........ A61Q 19/06; A61Q 19/04; A61Q 19/02; A61Q 19/007; C12N 1/20; A61K 35/74; A61K 2800/40
See application file for complete search history.

(56) References Cited

U.S. PATENT DOCUMENTS

2003/0049231 A1*  3/2003  Baur .................. A61K 8/99
                                                    424/93.4
2007/0166800 A1*  7/2007  Lin ..................... A61K 33/00
                                                    435/91.1
(Continued)

FOREIGN PATENT DOCUMENTS

WO    WO2004103332 A1    12/2004
WO    WO2008011884 A1    1/2008
WO    WO2010069335 A2    6/2010

OTHER PUBLICATIONS

Search Report and Written Opinion for PCT/US2016/029646 dated Jul. 4, 2016.

*Primary Examiner* — Jianfeng Song
(74) *Attorney, Agent, or Firm* — Brent M. Peebles

(57) ABSTRACT

The disclosure relates to topical compositions and methods comprising whole, non-viable Micrococcaceae cells, wherein the cells have been processed to kill the cells while minimizing lysis. The topical compositions and methods are useful for decreasing skin inflammation and improving skin barrier function.

13 Claims, 10 Drawing Sheets

(51) Int. Cl.
*A61K 35/74* (2015.01)
*A61Q 19/00* (2006.01)
*A61Q 7/00* (2006.01)
*A61Q 17/04* (2006.01)
*A61Q 19/02* (2006.01)
*A61Q 19/04* (2006.01)
*A61Q 19/06* (2006.01)
*A61Q 19/08* (2006.01)

(52) U.S. Cl.
CPC .... *A61K 2800/40* (2013.01); *A61K 2800/805* (2013.01); *A61K 2800/81* (2013.01); *A61Q 7/00* (2013.01); *A61Q 17/04* (2013.01); *A61Q 19/007* (2013.01); *A61Q 19/02* (2013.01); *A61Q 19/04* (2013.01); *A61Q 19/06* (2013.01); *A61Q 19/08* (2013.01)

(56) References Cited

U.S. PATENT DOCUMENTS

2012/0052093 A1* 3/2012 Bicalho .................. A61K 35/76
424/257.1
2014/0017182 A1* 1/2014 Trumbore ................ A61K 8/66
424/59
2015/0079040 A1* 3/2015 O'Neill .................... A61K 8/99
424/93.3

* cited by examiner

COMPOSITIONS AND METHODS FOR IMPROVING SKIN HEALTH

FIELD OF THE INVENTION

The disclosure relates to topical compositions and methods for improving skin health.

BACKGROUND OF THE INVENTION

Skin barrier function is essential for skin health and protects against chemical and biological insults from the outside environment. Skin attenuates the penetration of harmful radiation, including ultraviolet (UV) radiation, into deeper skin layers and prevents infection. Skin also acts as a permeability barrier and prevents loss of body moisture. Dysfunction of the skin barrier can lead to chronic skin conditions, disease, and in extreme cases, can even threaten the viability of the organism.

Topical compositions comprising extracts from bacteria have been described (see U.S. Patent Publication Nos. 20140335137 and 20140186433). For example, extracts of *Micrococcus luteus* comprising endonuclease, a DNA repair enzyme, have been used in compositions for sun-damaged skin. To prepare such compositions, cells are lysed to release the intracellular endonuclease, which is collected from the lysate and added to the composition. Lysis of the cells can be achieved using a number of methods, including the use of heat, chemicals (e.g., acid/base), enzymes (e.g., lysins, proteases, amylases), ultrasound, physical stress (e.g., pressure, homogenization, mechanical disruption; freeze/thaw cycling), radiation (e.g., gamma, ultraviolet), osmotic shock, viral infection, lytic gene expression, and others known in the art. Such methods for lysing cells cleave the bacterial cell wall and degrade the basic cell structure. The lysed cell wall and other structural components are typically separated from the endonuclease-containing portion of the lysate and discarded. Topical compositions comprising live *Micrococcus luteus* have also been described (see U.S. Patent Publication No. 20110189133). The live *Micrococcus luteus* cultures can compete with other skin flora to treat or prevent skin disorders associated with unwanted bacterial growth. However, delivery of live organisms to the skin can be challenging from a formulation and safety standpoint, especially in compromised skin.

Inflammation and its associated disruption of homeostasis can decrease skin barrier function. During an inflammatory response, cells of the immune system (e.g., lymphocytes and macrophages) and skin cells (e.g., Langerhans cells and keratinocytes) release cytokines, which can be pro-inflammatory (e.g., interleukin (IL)-1, IL-1α, IL-1β, IL-8, IL-12, IL-18, and TNF) or anti-inflammatory (e.g., IL-4, IL-1 receptor antagonist (IL-1Ra or IL-1RN, IL-10, IL-11, and IL-13). Compositions and methods for regulating cytokine production to treat and prevent inflammation provide a beneficial impact on skin barrier function and overall skin health and are continuing objectives in the personal care and cosmetic industry.

SUMMARY OF THE INVENTION

The disclosure relates to compositions and methods for improving skin health and appearance comprising applying whole, non-viable Micrococcaceae cells to the skin.

In one aspect, the disclosure provides a topical composition comprising whole, non-viable Micrococcaceae cells. The Micrococcaceae cells have been processed to kill the cells while minimizing lysis. The topical composition may further comprise other whole, non-viable Gram-positive bacteria cells in the family Micrococcaceae, such as bacteria from the genus *Kocuria*. In some embodiments, the topical composition further comprises a skin care agent selected from the group consisting of an anti-inflammatory agent, a probiotic, a probiotic-derived agent, a sunscreen/sunblock, an anti-acne agent, a retinoid, an emollient, a moisturizer, a desquamation agent, a humectant, an exfoliant, an anti-cellulite agent, a chelating agent, a self-tanning agent, an antioxidant, a hair growth regulator, an anti-wrinkle agent, a skin-lightening agent, an anti-atrophy agent, a mineral, a phytosterol, a plant hormone, a peptide, an anti-microbial agent, an anti-fungal agent, a prebiotic, a plant serum, a vitamin, and combinations thereof.

In another aspect, the disclosure provides a method of reducing skin inflammation comprising applying a composition comprising whole, non-viable Micrococcaceae cells to the skin of a subject. In one aspect, the composition described herein decreases the ratio of IL-1Ra to IL-1α in the skin, compared to untreated skin or skin treated with live or lysed Micrococcaceae cells. In another aspect, the composition described herein decreases the ratio of IL-1Ra to IL-1β in the skin, compared to untreated skin or skin treated with live or lysed Micrococcaceae cells. In related embodiments, the composition decreases measures of redness in skin after damage to the skin. In some embodiments, the composition improves skin health and appearance, e.g., by improving the barrier function of the skin, increasing the moisture content of the skin, and/or decreasing irritation.

In one aspect, the disclosure provides a method of increasing the anti-inflammatory activity of a population of Micrococcaceae cells comprising processing the cells to produce whole, non-viable cells. In some embodiments, the processed cells decrease IL-12p70 production and/or increase or maintain IL-10 production by Peripheral Blood Mononuclear Cells (PBMC) in vitro, thus increasing the ratio of IL-10/IL-12p70 in PBMCs exposed to whole, non-viable Micrococcaceae cells. In a related aspect, the disclosure provides a method of selecting bacterial modulators of skin barrier health for use in topical compositions based on their ability to affect specific in vitro biomarkers. In one aspect, the bacteria are selected for their ability to decrease IL-12p70 and/or maintain or increase IL-10 production in a PBMC model of inflammation.

In various embodiments, processing the bacterial cells to produce whole, non-viable cells comprises heating the cells at a temperature between about 60° C. and about 150° C. (e.g., about 80° C.), optionally for a time between about 30 seconds to about 45 minutes (e.g., about 30 minutes). In other embodiments, processing the bacterial cells to produce whole, non-viable cells comprises contacting the cells with a compound selected from the group consisting of a chaotrope, a detergent, an acidic solution, organic solvent, and combinations thereof. In still other embodiments, processing the bacterial cells to produce whole, non-viable cells comprises irradiating the bacteria with gamma, ultraviolet radiation or other ionizing radiation. In still other embodiments, processing the bacteria cells to selectively remove and/or denature a cell associated protein, pro-inflammation inducing protein without changing the whole intact nature of the cells. Where said protein is known to induce an IL12 response; thereby said processing preferentially increasing the anti inflammatory to pro-inflammatory ratio.

In some embodiments, the composition or population of Micrococcaceae cells comprises Micrococcaceae cells from the genus *Micrococcus* or *Kocuria*, optionally from at least one of the species *Micrococcus luteus, Micrococcus lylae, Kocuria kristinae, Kocuria rhizophila*, and *Kocuria varians*. In some embodiments, the composition or population of Micrococcaceae cells comprises cells from at least one *Micrococcus luteus* strain selected from, but not limited by, the group consisting of NRRL B-67034, NRRL B-67033, and strains identified as 3C, 133C, 173C, 157C, 183C, 66C, 55C, 243C, 50C, 119C and 59C.

Other features and advantages of the disclosure will become apparent from the following detailed description, including the drawings. It should be understood, however, that the detailed description and the specific examples, while indicating preferred embodiments, are provided for illustration only, because various changes and modifications within the spirit and scope of the invention will become apparent to those skilled in the art from the detailed description.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by selecting key elements for the purpose of more clearly showing other elements and illustrating a point of emphasis. Such selections of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

The disclosure provides methods for improving skin health comprising topically applying a composition comprising whole, non-viable Micrococcaceae cells to the skin of a subject. The disclosure also relates to methods of increasing the anti-inflammatory activity of Micrococcaceae cells and other Gram-positive bacteria cells comprising processing the cells, e.g., using heat, chemicals, and/or radiation, to produce whole, non-viable cells. In another aspect, the disclosure provides topical compositions comprising whole, non-viable Micrococcaceae cells. In another aspect, the disclosure provides a method of selecting bacterial modulators of skin barrier health for use in topical compositions based their ability to affect specific in vitro biomarkers, such as the ratio of IL-10/IL-12p70 produced by PBMC.

Figure 1A:
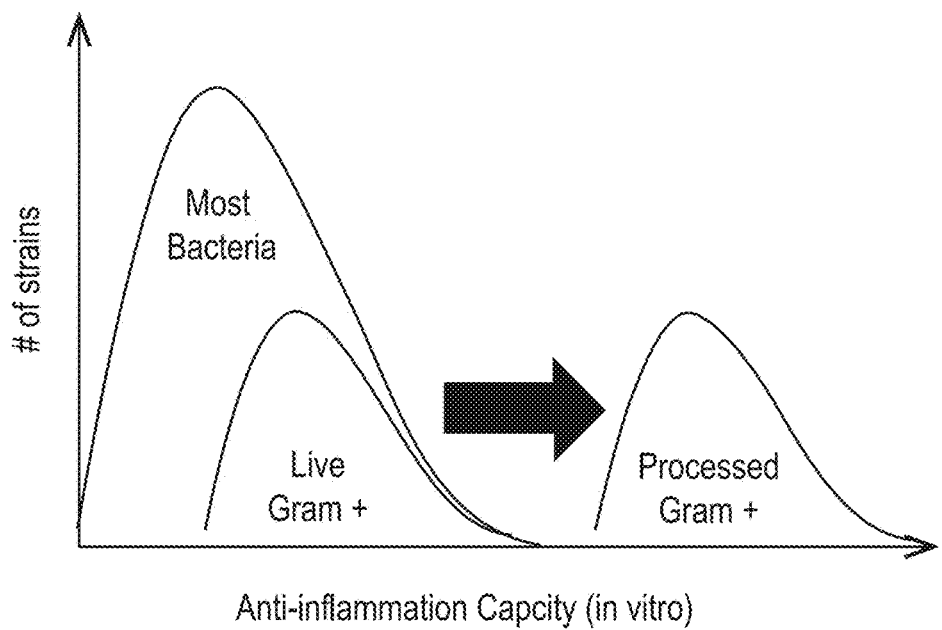
FIG. 1A depicts the anti-inflammation capacity of whole, non-viable (i.e., processed) Gram-positive bacteria compared to live Gram-positive bacteria and other bacteria.

The methods and compositions of the disclosure relate to whole, non-viable Micrococcaceae cells that have been processed in a manner that kills the cells while minimizing lysis. It has surprisingly been found that whole, non-viable Micrococcaceae cells have anti-inflammatory effects that are more pronounced than live Micrococcaceae cells (FIG. 1A). The whole, non-viable Micrococcaceae cells also have anti-inflammatory effects that are more pronounced than lysed or disrupted Micrococcaceae cells, such as cells processed using a French press, bead-beating or extreme chemistries (e.g., CTAC (Hexadecyltrimethylammonium chloride), or CTAB (Hexadecyltrimethylammonium bromide), which are examples of cationic surfactants). It will be appreciated that these processing affects are time and concentration dependent and can be optimized to maximize efficacy without destroying the cell. It will also be appreciated that aspects of the Micrococcaceae cells of various embodiments of the composition described herein also apply to the Micrococcaceae cells of various embodiments of the methods described herein.

In one aspect, the Micrococcaceae cells of the composition or method comprise cells belong to the genus *Micrococcus* and/or *Kocuria*, for example, *Micrococcus luteus* cells, *Micrococcus lylae* cells, *Kocuria kristinae* cells, *Kocuria rhizophila* cells, *Kocuria varians* cells, and combinations thereof. In various embodiments, the Micrococcaceae cells of the composition or method are from at least one *Micrococcus luteus* strain selected from, but not limited by, the group consisting of NRRL B-67034, NRRL B-67033, and strains identified in our internal library as 66C, 55C, 243C, 50C, 119C, 59C 3C, 133C, 173C, 157C, and 183C. In some embodiments, the Micrococcaceae cells of the composition or method comprise cells from *Micrococcus luteus* strain NRRL B-67034 or strain NRRL B-67033. In some embodiments, whole, non-viable Micrococcaceae cells (including those listed above) are selected for use in the compositions and methods of the disclosure based on their ability to demonstrate anti-inflammatory capacity in an in vitro screening assay (e.g., PBMC assay).

The following definitions may be useful in aiding the skilled practitioner in understanding the disclosure. Unless otherwise defined herein, scientific and technical terms used in the disclosure shall have the meanings that are commonly understood by those of ordinary skill in the art.

The terms "apply" and or "application," as used herein in reference to a composition refers to contacting a mammalian skin surface with a topical composition.

The term "dermatologically acceptable" as used herein refers to a composition or component thereof that may be used in contact with mammalian skin tissue without undue toxicity, incompatibility, instability, allergic response, and the like. The term "dermatologically acceptable carrier" as used herein refers to a carrier that is suitable for topical application to keratinous tissue, has acceptable aesthetic properties, is compatible with the active compounds, and does not cause any safety or toxicity concerns.

The terms "effective amount" and "safe and effective" as used herein refers to an amount of a compound or composition sufficient to induce a positive benefit without serious side effects (i.e., to provide a reasonable benefit-to-risk ratio, within the scope of sound judgment of the skilled artisan).

The term "facial skin surfaces" as used herein refers to one or more of forehead, peri-orbital, cheek, peri-oral, chin, neck and nose skin surfaces.

The term "improving skin health" as used herein refers to effecting a perceptible positive change or benefit in the appearance, texture, and/or function of skin. A perceptible positive change or benefit can include, for example, one or more of the following: preventing or reducing inflammation; improving skin barrier function; reducing skin redness/irritation; reducing the appearance of wrinkles, coarse deep lines, fine lines, crevices, bumps, blemishes and/or large pores; thickening of keratinous tissue; increasing the collagen and/or elastin content of the skin; lightening the skin; increasing skin elasticity; improving the coloration of the skin, for example, reducing under-eye circles, blotchiness, sallowness, dullness, and hyperpigmentation; and increasing moisture content of the skin.

The term "lyse" as used herein refers to perforating or breaking open a cell and/or structural component of a cell (e.g., cell wall, cell membrane, or cytoskeleton). A cell that has been lysed lacks its characteristic shape (e.g., spherical or elliptical) and/or some or all of its soluble intracellular contents. The term "minimizing lysis" refers to processing a population of cells in a manner such that only a small subset of the population are lysed, e.g., less than 25% of the cells, and a larger set of the population are whole, e.g., greater than 25%.

The term "non-viable" as used herein refers to a cell that is not reproducing, i.e., is not capable of reproduction. The presence of non-viable cells can be confirmed using methods known in the art, e.g., a colony forming assay to determine colony forming units (CFU) per unit of measure (milligram, milliliter, etc.) or dyes that differentially stain live and dead cells.

The term "stressor" as used herein refers to an environmental element that can cause skin inflammation and/or damage skin barrier function. Non-limiting examples of stressors include UV and other types of radiation, heat, cigarette smoke, ozone, engine exhaust, smog, microorganisms, seasonal dryness, and chemicals.

The term "topical composition" as used herein refers to a composition suitable for application to mammalian, e.g., human, skin. Non-limiting examples of topical compositions include skin care formulations such as cleansers (e.g., liquid, bar, gel, oil, or foam), toners, serums, masks, lotions, creams, ointments, balms, oils, scrubs, and treatments; as well as cosmetic products, including, but not limited to, foundations, eye liners, eye shadows, blushes, bronzers, highlighters, lip liners, brow pencils, blemish/beauty balm (BB) creams, color correcting/control (CC) creams, lipsticks, mascaras, lip glosses, lip balms, concealers, and powders. Topical compositions optionally regulate and/or improve various skin conditions or provide a desired visual effect. For example, a topical composition can provide one or more of the following effects: improve skin appearance and/or texture; increase the thickness of one or more layers of the skin; improve the elasticity or resiliency of the skin, improve the firmness of the skin; reduce the oily, shiny, or dull appearance of skin; improve the hydration status or moisture content of skin; minimize the appearance of fine lines or wrinkles; improve skin exfoliation or desquamation; plump the skin; soften the skin; improve skin barrier function; improve skin tone; reduce inflammation, redness or skin blotches or hyperpigmentation; and improve the brightness, radiance, or translucency of skin.

The term "whole" as used herein refers to a cell having the shape (e.g., spherical) of a live Micrococcaceae cell. A whole cell retains the cellular superstructure (e.g., the peptidoglycan layer in the cell wall) and is not fragmented. The presence of a whole cell phenotype can be confirmed using methods known in the art, such as microscopy or other imaging techniques or simply measuring the release of intracellular components. The cells are still considered whole even after the removal of cell associated protein surface proteins.

Strains have been deposited under conditions that assure that access to the culture will be available during the pendency of this patent application to one determined by the Commissioner of Patents and Trademarks to be entitled thereto under 37 C.F.R. §1.14 and 35 U.S.C. §122 and under conditions of the Budapest Treaty. The deposit represents a biologically pure culture of each deposited strain.

The following microorganisms as described herein have been deposited with the Agricultural Research Culture Collection (NRRL), Peoria, Ill. and have been assigned the following accession numbers:

*Micrococcus luteus* NRRL B-67034 and *Micrococcus luteus* NRRL B-67033

The present invention is not to be limited in scope by the microorganisms deposited, since the deposited embodiments are intended as single illustrations of one aspect of the invention and any which are functionally equivalent are within the scope of this invention. Indeed, various modifications of the invention in addition to those shown and described herein will become apparent to those skilled in the art from the foregoing description and accompanying Figures. Such modifications are intended to fall within the scope of the appended claims.

In one aspect, the disclosure provides topical compositions comprising whole, non-viable Micrococcaceae cells. The Micrococcaceae cells have been processed to kill the cells while minimizing lysis. The processed Micrococcaceae cells and compositions thereof have improved anti-inflammatory properties compared to live Micrococcaceae cells. Accordingly, in another aspect, the disclosure provides methods for increasing the anti-inflammatory activity of a population of Micrococcaceae cells comprising processing the cells to produce whole, non-viable cells.

The Micrococcaceae cells may be obtained and cultured from commercially available strains or from environmental samples before being processed as described herein. In one aspect, the composition comprises whole, non-viable Micrococcaceae cells that have been heated at a temperature of at least about 60° C., for example, between about 60° C. to about 150° C., between about 60° C. to about 80° C., between about 70° C. to about 90° C., or between about 65° C. to about 100° C. In various aspects, the cells have been heated at a temperature of about 60° C., about 65° C. about 70° C., about 75° C., about 80° C., about 85° C., about 90° C., about 95° C., about 100° C., or up to and including about 150° C. The heating can be performed using any of a number of means, such as a water bath, oil bath, thermal cycler, incubator, oven, and any other means known in the art. The heating is conducted for a length of time sufficient to produce whole, non-viable cells, for example, about 30 minutes to about 45 minutes, about 10 minutes to about 30 minutes, about 20 minutes to about 45 minutes, about 25 minutes to about 40 minutes, or more than 60 minutes. In various embodiments, the cells have been heated for about 5 minutes, about 10 minutes, about 15 minutes, about 20 minutes, about 25 minutes, about 30 minutes, about 35 minutes, about 40 minutes, about 45 minutes, or about 60 minutes. In one aspect, the composition comprises cells that have been heated at a temperature between about 60° C. to about 90° C. for about 30 minutes.

Any temperature and time combination that produces a whole, non-viable Micrococcaceae cell is contemplated. The temperature necessary to process the cell depends heavily on the time, and the amount of heating time necessarily will depend on the temperature. For reasonable times of several minutes to an hour, a minimum temperature of about 60° C. is generally required. For shorter times, a higher temperature is required; temperatures lower than 60° C. may be used with appropriately long exposure times. The temperature used can thus be very high, if the time at that temperature is miniscule. Therefore, there is no maximum temperature, other than what might be practical at industry scale (e.g., about 150° C. to about 200° C.). The concept of "Equivalent Point Method" (see, e.g., U.S. Pat. No. 7,833,561), which includes all temperature and times that provide equivalent efficacy to those provided herein for producing whole, non-viable cells, is applicable to the compositions and methods of the disclosure.

Heat is used to kill the cells while minimizing lysis, as described above, generating whole, non-viable cells. Whole non-viable cells are produced by the application of heat over time and by this process the cells are heat killed (HK), heat activated (HA) or heat processed (HP). Isolates and strains are designated with numbers and letters to distinguish within the bacteria library (e.g. 173 or 173C). In another aspect, the composition comprises whole, non-viable Micrococceacea cells that have been contacted with a cytotoxic compound. In one aspect, the cytotoxic compound is selected from the group consisting of a chaotrope, an anionic detergent, a zwitterionic detergent, a cationic detergent, a nonionic detergent, an organic solvent, an acidic solution, and combinations thereof. The cells are contacted with the cytotoxic compound for a length of time sufficient to kill the cells without lysing them, for example, about 1 minute, about 2 minutes, about 3 minutes, about 4 minutes, about 5 minutes, about 6 minutes, about 7 minutes, about 8 minutes, about 9 minutes, about 10 minutes, or more. In one aspect, the cytotoxic compound is a nonionic chaotrope such as guanidine HCl, urea, thiourea, phenol, glycine, formamide, or acetamide. In another aspect, the cytotoxic compound is an ionic chaotrope that contains large singly charged ions with low charge density, such as $SCN^-$, $ClO_4^-$, $I^-$, or $Br^-$. Examples of ionic chaotropes include, but are not limited to, lithium chloride, lithium perchlorate, lithium acetate, and magnesium chloride. In one aspect, the detergent is an anionic, non-ionic, or zwitterionic surfactant. Examples of anionic surfactants include, but are not limited to sodium cholate, sodium dodecyl sulfate (SDS), lithium dodecyl sulfate, sodium deoxycholate, sodium N-lauroylsarcosinate, chenodeoxycholic acid, sodium chenodeoxycholate, sodium glycocholate, sodium glycodeoxycholate, sodium glycolithocholate, sodium glycoursodeoxycholate, sodium lauroylsacrosinate, sodium taurochenodeoxycholate, sodium taurocholate, sodium taurodeoxycholate, sodium tauroursodeoxycholate, and sodium ursodeoxycholate. Examples of non-ionic surfactants include, but are not limited to, n-Dodecyl-b-D-maltoside, Octyl-b-D-glucopyranoside, Octyl-b-D-thioglucopyranoside, Polyoxyethylene (20) sorbitan monolaurate (TWEEN 20), TWEEN 40, TWEEN 60, TWEEN 80, TWEEN 85, Saponin, polyethylene glycol mono-4-octylphenyl ether n~23, polyethylene glycol monocetyl ether n~23, polyethylene glycol monododecyl ether n~25, Triton X-100, Triton X-114, NP-40, APO-10, APO-12, Big CHAP, BRIJ® 35, C12E8, C12E9, Cyclohexyl-n-hexyl-b-D-maltoside, n-Decanoylsucrose, n-Decyl-b-D-maltopyranoside, Digitonin, n-Dodecanoylsucrose, GENAPOL® C-100, GENAPOL® X-080, GENAPOL® X-100, HECAMEG, n-Heptyl-b-D-glucopyranoside, n-Heptyl-b-D-thioglucopyranoside, n-Hexyl-b-D-glucopyranoside, MEGA-8, MEGA-9, MEGA-10, n-Nonyl-b-D-glucopyranoside, n-Octanoylsucrose, n-Octyl-b-D-maltopyranoside, and PLURONIC® F-127. Examples of zwitterionic surfactants include, but are not limited to, aminosulfobetaine-14, C7BzO, CHAPS (3-[(3-Cholamidopropyl)dimethylammoniol]-1-propanesulfonate), 3-(decyldimethylamonio)propane sulfonate, lauryl sulfobetaine, caprylyl sulfobetaine, n-octyl sulfobetaine, palmityl sulfobetaine, myristyl sulfobetaine, Aminosulfobetaine-14-4, Aminosulfobetaine-16, Aminosulfobetaine-C6Ø, Aminosulfobetaine-C8Ø, CHAPSO, DDMAB, DDMAU, PMAL-B-100, ZWITTERGENT® 3-08, ZWITTERGENT® 3-10, ZWITTERGENT® 3-12, ZWITTERGENT® 3-14, and ZWITTERGENT® 3-16. For example, in various aspects, the cells are processed with 8M guanidine, 4% (v/v) CHAPS, or 40 mM Octyl thioglucopyranoside, for about 5 minutes. In another aspect, the cytotoxic compound is an acidic solution, optionally having a pH of less than about 4. Examples of acidic solutions include, but are not limited to, phosphate buffer, citrate buffer, formate buffer, acetate buffer, propionate buffer, sulfonate buffer, chloroacetate buffer, trifluoroacetate buffer, and combinations thereof. In another aspect, solvents such as Methanol and/or Isopropanol may be used. In another aspect, extreme chemistries may be used (e.g., cationic surfactants such as CTAC (Hexadecyltrimethylammonium chloride), or CTAB (Hexadecyltrimethylammonium bromide)).

In another aspect, the composition comprises whole, non-viable Micrococcaceae cells that have been irradiated, e.g., with gamma or UV radiation. The irradiation is conducted for a length of time sufficient to produce whole, non-viable cells, for example, to provide a dosage of about 17 kiloGrays to about 22 kiloGrays.

Other methods that produce whole, non-viable Micrococcaceae cells are also contemplated, including the use of controlled pressure or other cytotoxic compounds. So long as the treatment is sufficient to kill the cells while minimizing lysis, i.e., to produce whole, non-viable Micrococcaceae cells, such methods are within the scope of the present disclosure.

The integrity and viability of the processed Micrococcaceae cells can be determined using any of a number of methods, such as microscopy, dye exclusion, and others known in the art, to confirm that the bacterial cells are whole and non-viable.

In one aspect, the whole, non-viable Micrococcaceae cells of the composition and methods decrease the production of a pro-inflammatory cytokine and/or increase the production of an anti-inflammatory cytokine by an immune system cell or skin cell. One method of measuring cytokine production in vitro is the PBMC assay (see, e.g., Friberg et al., Clin Diag Lab Immunology; 1994; 1(3):261-268) or US 2010/0183559). Generally, human PBMC are isolated from blood and incubated with a test substance (e.g., a bacterial suspension) in media, e.g., for 24 hours. The release of cytokines from the PBMC is measured following incubation. Any of a number of methods can be used to identify and quantify the cytokines released from the PBMC, such as enzyme-linked immunosorbent assays (ELISA), radioimmunoassays, bead arrays, and others known in the art.

In one aspect, the whole, non-viable Micrococcaceae cells of the disclosure decrease the production of IL-12p70 more than live Micrococcaceae cells, optionally by at least about 10%, at least about 20%, at least about 30%, at least about 40%, at least about 50%, at least about 75%, at least about 100%, or more. In another aspect, the whole, non-viable Micrococcaceae cells decrease the IL-12p70 production by PBMC in vitro to less than 70 pg/mL, for example, less than 65 pg/mL, less than 60 pg/mL, less than 55 pg/mL, or less than 50 pg/mL, wherein a milliliter comprises $2.0 \times 10^5$ PBMC.

In one aspect, the whole, non-viable Micrococcaceae cells of the disclosure decrease the production of IL-12p70 more than do live Micrcoccaceae. The decrease is a result of activation by the any of the methods described herein, including via application of a chaotrope, a detergent, an acidic solution, an organic solvent, or heat and combinations thereof. The activation of Micrococcaceae may also be identified by the loss—as determined by MALDI-TOF mass spectrometry—of a protein or peptide with greater than 40% sequence identity to SEQ ID 1, with greater than 50% sequence identity to SEQ ID 1, or with greater that 60% sequence identity to SEQ ID 1. The loss of a pro-inflammatory protein upon heating is demonstrated in FIG. 1C, and the protein level is measured in the supernatant, for example a protein as shown by SEQ ID 1. The protein level is low in the supernatant of the live cells. After heat treatment the protein level in the supernatant is high indicating that the protein, identified as being responsible for the production of IL-12p70 in PBMC, is disassociated from the cell upon heat activation.

In a further aspect whole, non-viable *Micrococcus luteus* cells of the disclosure decrease the production of IL-12p70 more than do live *Micrococcus luteus* cells when activated by any of the methods described herein, including via application of a chaotrope, a detergent, an acidic solution, an organic solvent, or heat and combinations thereof. The activation of *Micrococcus luteus* cells may be identified by the loss—as determined by MALDI-TOF mass spectrometry—of a protein or peptide with greater than 90% sequence identity to SEQ ID 1, with greater than 95% sequence identity to SEQ ID 1, or with greater than 97% sequence identity to SEQ ID 1.

In a further aspect, upon heat activation of the Micrcoccaceae, the peptide of SEQ ID 1 is dissociated from the cell matrix and can be detected in a cell wash supernatant.

```
SEQ ID 1:
GIGDLNNLAN QHSDKINEAV DNAQEQHGDK LGEHGDTVNK
GVDGAQEKFL SGDEGEQQA
```

Alternatively or in addition, the whole, non-viable Micrococcaceae cells of the disclosure maintain or increase the production of IL-10 more than live Micrococcaceae cells or lysed Micrococcaceae cells. Production of IL-10 is optionally increased by at least about 10%, at least about 20%, at least about 30%, at least about 40%, at least about 50%, at least about 75%, at least about 100%, or more, compared to live bacteria or lysed bacteria cells. In one aspect, the whole, non-viable Micrococcaceae cells increase the IL-10 production of PBMC in vitro to greater than 1000 pg/mL, for example, greater than 1500 pg/mL, greater than 2000 pg/mL, greater than 2500 pg/mL, or greater than 3000 pg/mL, wherein a milliliter comprises $2.0 \times 10^5$ PBMC. Optionally, the whole, non-viable Micrococcaceae cells of the disclosure increase the ratio of IL-10 to IL-12p70 (IL-10/IL-12) produced by immune system cells (e.g., PBMC), preferably to a greater extent than live Micrococcaceae cells or lysed Micrococcaceae cells. For example, whole, non-viable Micrococcaceae cells increase the ratio of IL-10/IL-12p70 optionally in a range of between about 10% and about 1000%, compared to live bacteria or lysed bacteria cells.

Figure 1B:
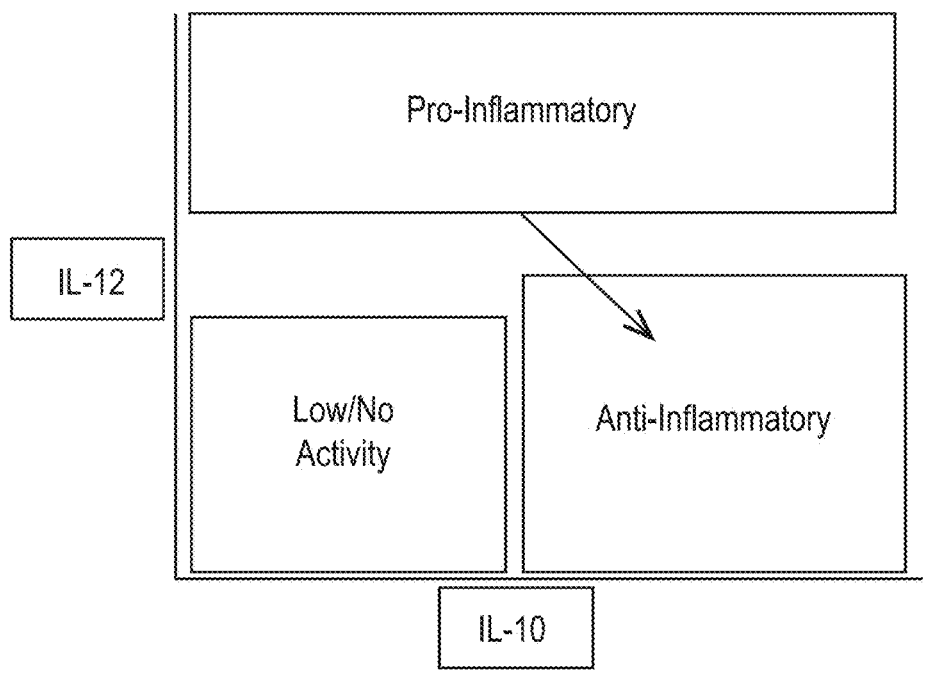
FIG. 1B depicts the ratio of anti inflammatory to pro-inflammatory effects indicated by the IL-10/IL-12p70 ratio.
Figure 1C:
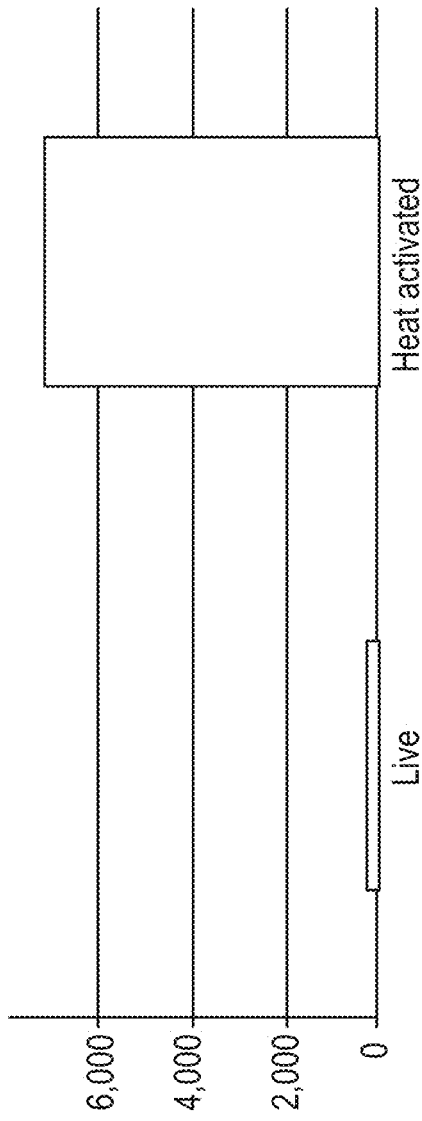
FIG. 1C depicts the level of a surface cell associated m/z 6244 protein in the supernatant of live *M luteus* cells, and of *M. luteus* cells after heat treatment, as detected by mass spectrometry.

In one aspect, whole, non-viable Micrococcaceae cells increase the ratio of IL-10/IL-12p70 produced by PBMC in vitro to at least 5:1, for example, to a ratio of about 5:1, about 10:1, about 15:1, about 30:1, about 100:1, about 300:1, or more, compared to live bacteria or lysed bacteria cells. A higher IL-10/IL-12p70 ratio indicates greater anti-inflammatory activity and thus higher capacity for anti-inflammatory effects in the skin (FIG. 1B).

In one aspect, the disclosure provides methods for increasing the anti-inflammatory activity of a population of Micrococcaceae cells comprising processing the cells to produce whole, non-viable cells. The methods of processing Micrococcaceae cells to produce whole, non-viable cells described herein can also be used to increase the anti-inflammatory activity of Gram-positive bacteria cells, such as cells belonging to the genus *Kocuria*. Gram-positive bacteria cells have a thick (20 nm to 80 nm) peptidoglycan layer in the cell wall that withstands degradation, allowing for certain cells to be killed while minimizing lysis, resulting in the production of whole, non-viable cells.

In another aspect, the disclosure provides a method of selecting bacterial modulators of skin barrier health for use in topical compositions based on their ability to affect specific in vitro biomarkers. In one aspect, the method comprises measuring cytokine production by PBMC in vitro and selecting bacteria that increase the ratio of IL-10/IL-12. In another aspect, the method comprises selecting bacteria that decrease the IL-12 production by PBMC in vitro. The MALDI-TOF can therefore be used as a means of identifying microbes that upon processing have reduced cell associated pro-inflammation proteins. In another aspect, the method comprises selecting bacteria that maintain the production of IL-10 by PBMC in vitro or increase the production of IL-10 by PBMC in vitro.

Topical compositions comprising whole, non-viable Micrococcaceae cells of the disclosure may be made into a wide variety of product forms that include, but are not limited to, solutions, suspensions, emulsions, lotions, creams, gels, ointments, balms, toners, sticks, pencils, sprays, aerosols, ointments, pastes, foams, powders, mousses, wipes, strips, patches, and masks. The foregoing product forms may be provided to a consumer as a skin care product for the face and/or body, including, but not limited to, cleansers (e.g., liquid, bar, oil, or foam), toners, serums, masks, lotions, creams, ointments, balms, oils, scrubs, and treatments. Embodiments of the disclosure may also be provided as a cosmetic product, including, but not limited to, foundations, eye liners, eye shadows, blushes, bronzers, highlighters, lip liners, brow pencils, blemish/beauty balm (BB) creams, color correcting/control (CC) creams, lipsticks, mascaras, lip glosses, lip balms, concealers, and powders.

The composition optionally comprises a dermatologically acceptable carrier. The composition form may follow from the particular dermatologically acceptable carrier chosen. The dermatologically acceptable carrier may contain one or more dermatologically acceptable solid, semi-solid, or liquid fillers, diluents, solvents, extenders, and the like. The dermatologically acceptable carrier can be inert or can itself possess dermatological benefits of its own. Suitable dermatologically acceptable carriers include conventional or otherwise known carriers. The dermatologically acceptable carrier is physically and chemically compatible with the processed cells described herein and should not unduly impair stability, efficacy or other benefits associated with the compositions of the disclosure.

The dermatologically acceptable carrier can be provided in a wide variety of solid, semi-solid, or liquid forms. Non-limiting examples include simple solutions (aqueous or oil-based), emulsions, and solid forms (e.g., gels, sticks, balms).

In one aspect, the topical compositions of the disclosure comprise whole, non-viable Micrococcaceae cells in an amount of between about $1 \times 10^7$ cells/mL and $5 \times 10^{10}$ cells/mL, or between about $5 \times 10^7$ cells/mg and $5 \times 10^{10}$ cells/mg, depending on the composition.

The composition of the disclosure optionally further comprises one or more of the following agents: anti-inflammatory agents, sunscreens or sunblocks, anti-acne agents, retinoids, emollients, moisturizers, desquamation agents, humectants, exfoliants, anti-cellulite agents, chelating agents, self-tanning agents, non-vitamin antioxidants and radical scavengers, hair growth regulators, anti-wrinkle agents, skin-lightening agents, anti-atrophy agents, minerals, phytosterols, plant hormones, peptides, vitamins, antimicrobial agents, anti-fungal agents, prebiotics, probiotics, probiotic-derived agents, plant serums, and other useful skin care and cosmetic agents known in the art.

The composition of the disclosure may also comprise one or more of a wide variety of cosmetic and pharmaceutical ingredients used in skin care and cosmetic products, for example, as described in the Personal Care Product Council's International Cosmetic Ingredient Dictionary and Handbook, 14$^{th}$ Edition (2012), incorporated herein by reference. Examples of such ingredients include, but are not limited to, abrasives, absorbents, acids, aesthetic components (e.g., fragrances, pigments, dyes), essential oils, anti-caking agents, anti-foaming agents, binders, biological additives, buffering agents, bulking agents, chemical additives, astringents, biocides, denaturants, emollients, analgesics, natural extracts, film formers or materials, oils, opacifying or luminescent agents, polymers, pH adjusters, preservatives, propellants, reducing agents, sequestrants, skin cooling agents, skin protectants, stabilizers, surfactants, thickeners, viscosity modifiers, waxes, and combinations thereof.

The composition of the disclosure generally is prepared by conventional methods known in the art. Such methods typically involve mixing the ingredients in one or more steps to a relatively uniform state, optionally with heating, cooling, application of vacuum, and the like. The composition is preferably prepared so as to optimize stability (physical stability, chemical stability, and/or photostability) and/or delivery of the active materials. The optimization may include appropriate pH (e.g., less than 7), exclusion of materials that can complex with the active agent(s) and negatively impact stability or delivery, use of approaches to prevent complex formation (e.g., appropriate dispersing agents or dual compartment packaging), selection of materials that are compatible with and will not modify the activity (e.g., surface activity) of the Micrococcaceae cells, use of appropriate photostability approaches (e.g., incorporation of sunscreen/sunblock or use of opaque packaging), and the like.

In some aspects, the composition is provided in a package sized to store a sufficient amount of the composition for the treatment period or in individual doses. The size, shape, and design of the packages may vary widely and are known in the art.

Whole, non-viable Micrococcaceae cells and topical compositions thereof may be used in methods of improving skin health, for example, by reducing skin inflammation and improving skin barrier function.

In one aspect, the disclosure provides a method of reducing skin inflammation. The method comprises applying whole, non-viable Micrococcaceae cells or a composition thereof to the skin of a subject. The Micrococcaceae cells have been processed to kill the cells while minimizing lysis. Any of the composition components described above may be used in the context of the methods described herein.

Many methods exist for characterizing inflammation in the skin. For example, the ratio of IL-1Ra to IL-1α in the skin can be measured before and after applying the whole, non-viable Micrococcaceae cells (or a composition thereof) to detect and measure the anti-inflammatory effect on skin evidenced by a decrease in the IL-1Ra/IL-1α ratio. In one aspect, applying the whole, non-viable Micrococcaceae cells or a composition thereof to the skin decreases the ratio of IL-1Ra/IL-1α produced in the skin, compared to untreated skin or skin processed with live or lysed Micrococcaceae cells. For example, the ratio of IL-1Ra/IL-1α produced in the skin optionally decreases by at least about 10%, at least about 15%, at least about 20%, at least about 30%, or more, compared to untreated skin or skin processed with live or lysed Micrococcaceae cells.

In one aspect, applying the whole, non-viable Micrococcaceae cells or composition thereof of the disclosure improves the barrier function of the skin, e.g., by decreasing skin permeability and/or increasing skin resistance to stressors. Methods and instruments for measuring skin barrier function, moisture content, and degree of redness and/or irritation are known in the art. For example, applying the whole, non-viable Micrococcaceae cells decreases transepidermal water loss (TEWL) or visually graded redness after insult to the stratum corneum, by, e.g., at least about 10%, at least about 20%, at least about 30%, at least about 40%, or more, compared to untreated skin or skin processed with live or lysed Micrococcaceae cells. In another example, applying the whole, non-viable Micrococcaceae cells decreases the skin surface redness measured by instruments such as the Chroma Meter® (Minolta) and TiVi700 (WheelsBridge) as an indicator of improved barrier function. These instruments measure the light coming off of the skin, and applying the whole, non-viable Micrococcaceae cells or composition thereof decreases measured redness, optionally by at least 10%, at least about 20%, at least about 30%, at least about 40%, or more, compared to untreated skin or skin processed with live or lysed Micrococcaceae cells. In another aspect, applying the whole, non-viable Micrococcaceae cells or composition thereof increases the moisture content of the skin. For example, the moisture content of the skin may be increased by at least 10%, at least about 20%, at least about 30%, at least about 40%, or more, compared to untreated skin or skin processed with living Micrococcaceae or lysed Micrococcaceae. In another aspect, applying the whole, non-viable Micrococcaceae cells or combination thereof decreases skin irritation.

Skin surfaces of the most concern tend to be those typically exposed to the environment, such as facial skin surfaces, hand and arm skin surfaces, foot and leg skin surfaces, and neck and chest skin surfaces. In some embodiments, compositions of the disclosure are applied to facial skin surfaces, such as the forehead, peri-oral region, chin, peri-orbital region, nose, and/or cheek skin surfaces. In some embodiments, compositions of the disclosure are applied to a site of irritation or injury. In some embodiments, the methods of processing skin further comprise improving or preventing the appearance of wrinkles, fine lines, coarse deep lines, crevices, bumps, large pores, hyperpigmentation, dullness, age spots, skin dryness, loss of skin elasticity, skin sagging, loss of skin recoil, loss of skin firmness, blotchiness, sallowness, blemishes and combinations thereof.

In one aspect, the methods of the disclosure comprise applying a composition comprising whole, non-viable Micrococcaceae cells to the skin surface. In some embodiments, the composition is chronically applied to the skin. The composition may be applied at least once a week, once a day, twice a day, or on a more frequent basis, during a treatment period. In some embodiments, the treatment period is between about one week and about twelve weeks. In some embodiments, the treatment period is between about four weeks and about twelve weeks. In some embodiments, the treatment period is between about four weeks and about eight weeks. In some embodiments, the treatment period will extend over multiple months (e.g., about three to about twelve months) or multiple years.

In some embodiments, the composition is applied once a day during the treatment period, for example, in the morning or before sleeping. In some embodiments, the composition is applied twice a day during the treatment period. When applied twice daily, the first and second applications may be separated by about one to about sixteen hours. For example, the composition may be applied in the morning after waking and in the evening before sleeping. In some embodiments, the composition is applied and massaged into the skin. The composition can also be applied so that it remains visible on the surface of the skin, e.g., for a cosmetic composition. The composition may be applied broadly, e.g., to one or more skin surfaces, or the application may be localized such that the composition is delivered to a targeted area while minimizing delivery to other skin surfaces. For example, the composition may be applied to a discrete area, such as a site of injury, or to a specific region, such as the cheek.

In some embodiments, a safe and effective amount of the composition from about 0.005 mg/cm$^2$ (milligrams of composition per square centimeter of skin) to about 0.01 mg/cm$^2$ is applied. In some embodiments, a safe and effective amount of the composition from about $2\times10^6$ CFU/cm$^2$ (milligrams of composition per square centimeter of skin) to about $2\times10^8$ CFU/cm$^2$ is applied (CFU are determined from live bacteria stocks before processing). In some embodiments, the method comprises applying a composition in the form of a skin lotion, skin cream, or cosmetic product, which is intended to be left on the skin for some esthetic, prophylactic, therapeutic or other benefit. After applying the composition to a skin surface, the composition may be left on the skin for a period of at least about 15 minutes, or at least about 30 minutes, or at least about one hour.

In some embodiments, the composition may be delivered by a variety of applicators appropriate for general and/or localized application. Examples of such applicators include, but are not limited to, droppers, wands, swabs, brushes, sponges, pads, balls, puffs, pens or any other suitable device. In some embodiments, the composition is applied directly using the hand or in other conventional manners known in the art.

The treatment period and/or application frequency should be sufficient to provide an improvement in skin health, e.g., decreasing or preventing inflammation or improving skin barrier function.

The present disclosure will be more readily understood by reference to the following Examples, which are provided by way of illustration and are not intended to be limiting.

Example 1

Micrococcaceae cells were obtained from skin swab cultures or purchased (ATCC) and grown in tryptic soy broth (TSB, formula available in the art or available commercially; Hardy Diagnostics) (ranges: 33-37° C., 18-24 h, 150-200 rpm; orbital shaker) and collected at a speed sufficient to pellet by centrifugation (e.g. Sorvall Evolution Centrifuge; 12,000×g RCF, 10 min) Cell pellets were washed in phosphate buffered saline (PBS; standard formula common in the art; e.g. Dulbecco's Ca and Mg free) and resuspended in a normalized volume using the OD 600. This is a 100% stock of Micrococcaceae cells. Heat was used to kill the cells while minimizing lysis, generating whole, non-lysed cells. Small diameter thin-wall NMR tubes (5 mm economy NMR tube 7", Wilmad LabGlass) were filled with a suspension of the Micrococcaceae cells and flame-sealed while the tubes were kept in an ice-bath. The sealed tubes were completely immersed in a circulating water bath (Lauda Brinkmann) Two thermocouples type T (Omega Engineering Inc.) were used to measure the temperature at the center of the tube and the external water bath temperature. The thermocouples were connected to a 16-Channel Thermocouple Input Module (National Instruments, Model NI 9213). The tubes were heated at 60° C., 65° C., 70° C., 75° C. or 80° C. for up to 30 minutes. After removing the tubes from water bath, the tubes were quickly transferred to an ice-water slush container for fast cooling.

The effect of the heat-processed cells on IL-10 and IL-12p70 production was assessed using the PBMC assay. PBMC were isolated from human blood and maintained at 37° C., 5% $CO_2$. The PBMC were plated in 96-well plates at a density of $2\times10^5$ cells per well. The processed Micrococcaceae cells ($6.25\times10^6$ cells in 20 µL) were added to the PBMC-containing wells, and the well contents were mixed using a micro-plate shaker. The plates were incubated at 37°

C., 5% $CO_2$ for 24 hours. The supernatants were harvested and the cytokine content for example IL-10 or IL-12p70, was measured using a commercial ELISA or Bead Based kit (e.g. Meso Scale Discovery, Millipore).

Figure 2A:
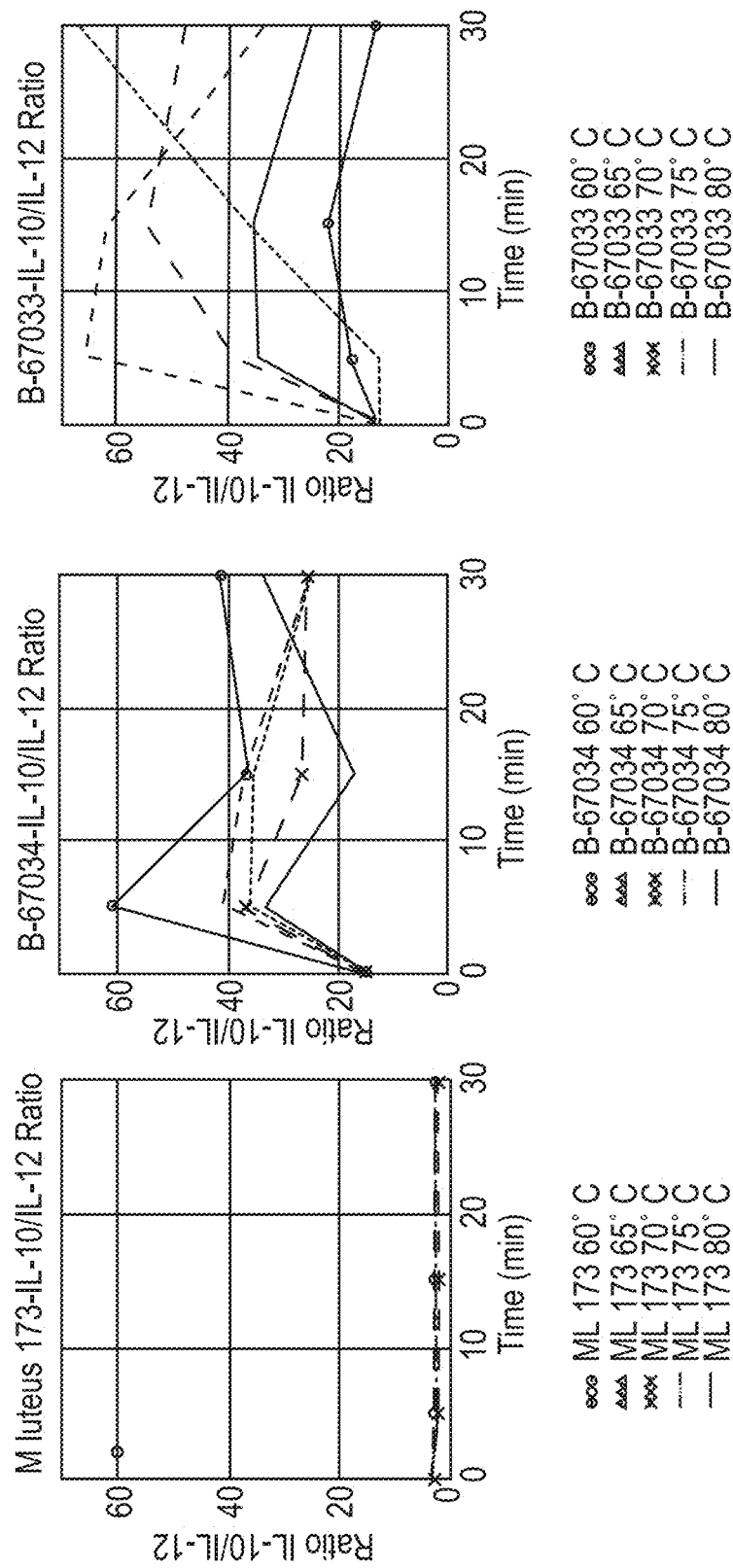
FIG. 2A depicts the ratio of IL-10/IL-12p70 measured using the PBMC assay for *M. luteus* strains NRRL B-67033 and strains identified as 173C and NRRL B-67034, and heated at 60° C. to 80° C. for up to 30 minutes.
Figure 2B:
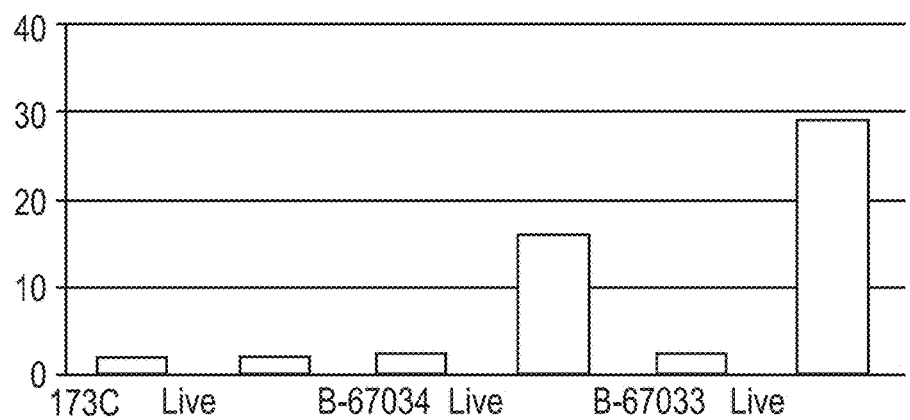
FIG. 2B depicts the IL-10/IL-12p70 ratio for live and heat-killed (HK) 173C, NRRL B-67034, and NRRL B-67033 cells.
Figure 2C:
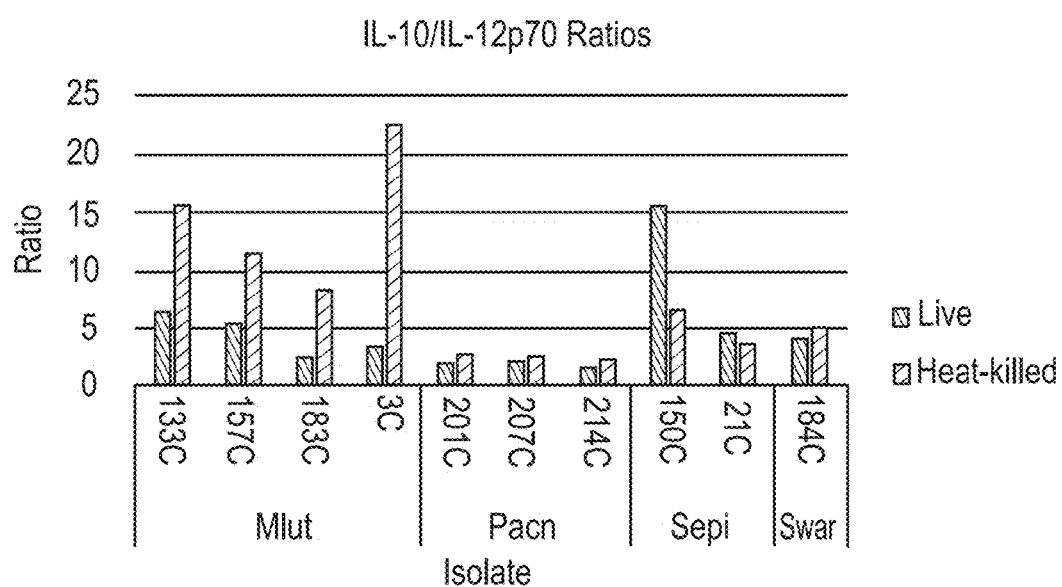
FIG. 2C depicts the IL-10/IL-12p70 ratios for live and heat-killed (80° C., 30') *M. luteus* (Mlut), *P. acnes* (Pacn), *S. epidermidis* (Sepi), and *S. warneri* (Swar) cells.
Figure 2D:
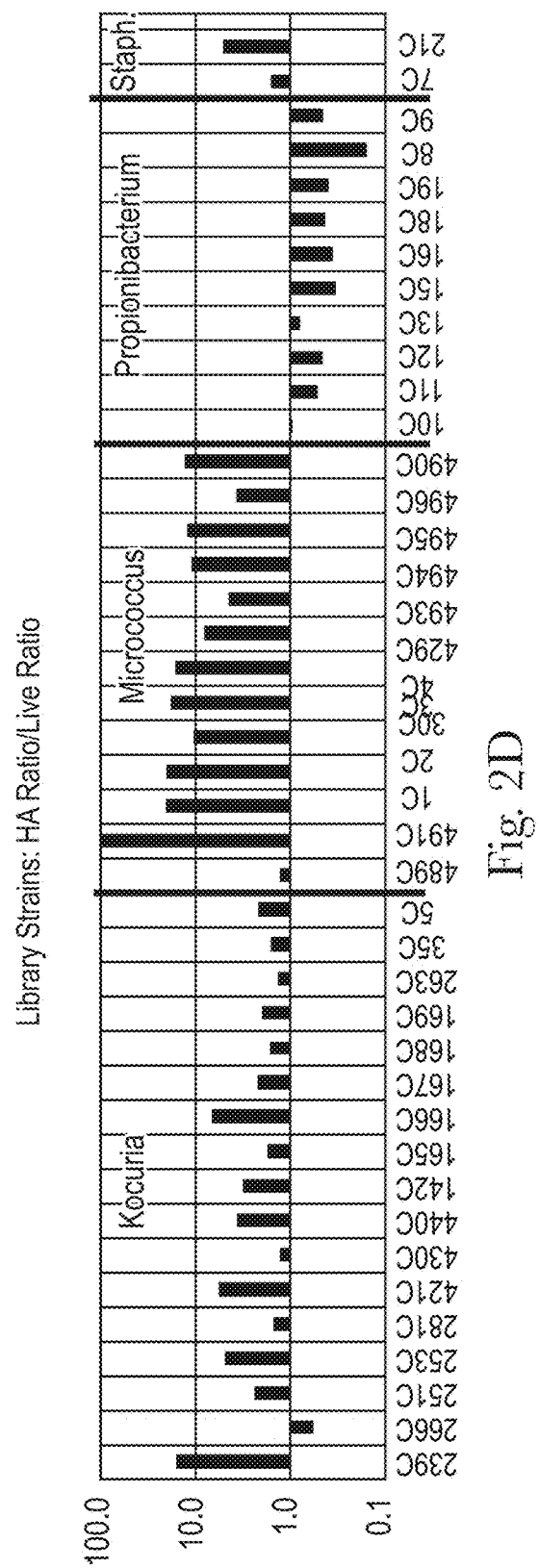
FIG. 2D depicts the IL-10/IL-12 ratio for heat-activated (HA) library strains divided by the IL-10/IL-12p70 ratio for *Kocuria, Micrococcus, P. acnes*, and *Staphylococcus* live cells.
Figure 2E:
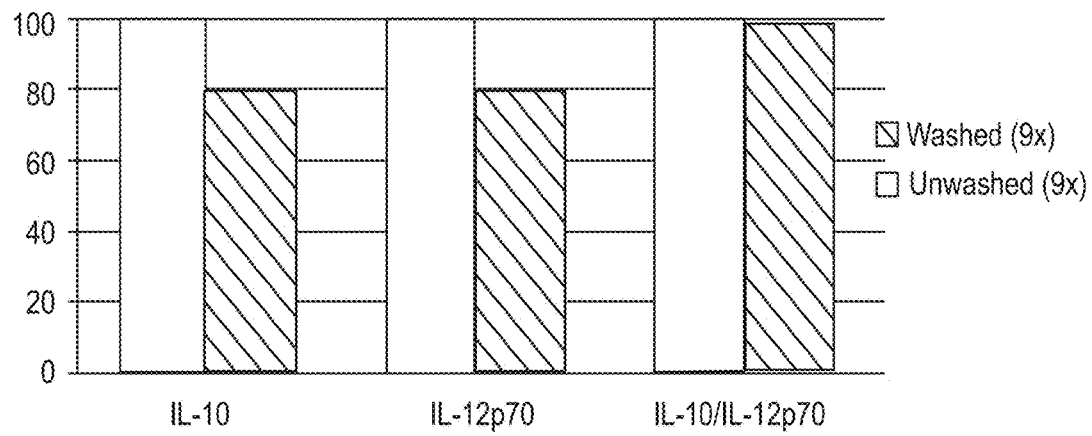
FIG. 2E depicts the IL-10/IL-12p70 ratio for *M. luteus* NRRL B-67034 cells that were heat-processed and then washed 9 times or unwashed.

Heat-processed *Micrococcus luteus* cells from strain NRRL B-67034 or NRRL B-67033 increased the IL-10/IL-12 ratio measured using the PBMC assay, compared to no heat processing (FIG. 2A). Strain 173C is shown as an example of a *Micrococcus luteus* that is less effective at increasing the IL-10/IL-12 ratio. For NRRL B-67034 cells, heat-processing increased the IL-10/IL-12 ratio more than five-fold compared to live NRRL B-67034 cells, and for NRRL B-67033 cells, heat-processing increased the IL-10/IL-12 ratio more than 10-fold compared to live NRRL B-67033 cells (FIG. 2B). An increase in the IL-10/IL-12 ratio measured using the PBMC assay for heat-processed cells compared to live cells was also observed in multiple strains of *Micrococcus* and *Kocuria* (FIGS. 2C and 2D). The increase in IL-10/IL-12 was maintained after heat-processed cells were washed (FIG. 2E).

Example 2

Micrococcaceae cells were processed using cytotoxic compounds to kill the cells while minimizing lysis. Briefly, a suspension of live Micrococcaceae cells was washed in PBS (as described in Example 1). The cell suspension (100% as described in Example 1) was pipetted into a microcentrifuge tube, which was centrifuged (12,000×g rcf for 1 minute) to pellet the cells. The supernatant was removed and discarded. The cytotoxic compound in media was pipetted into the tube containing the cell pellet. The tube was vortexed until the cells were fully resuspended and then incubated at room temperature for 5 minutes.

Following treatment, the tube was centrifuged to pellet the cells (12,000×g rcf for 1 minute), and the supernatant was discarded. To wash the cells, the cells were suspended in saline solution (0.9% w/v or normal saline) by vortexing and then centrifuged again to pellet the cells. The supernatant was discarded. The washing step was repeated twice more.

Figure 3:
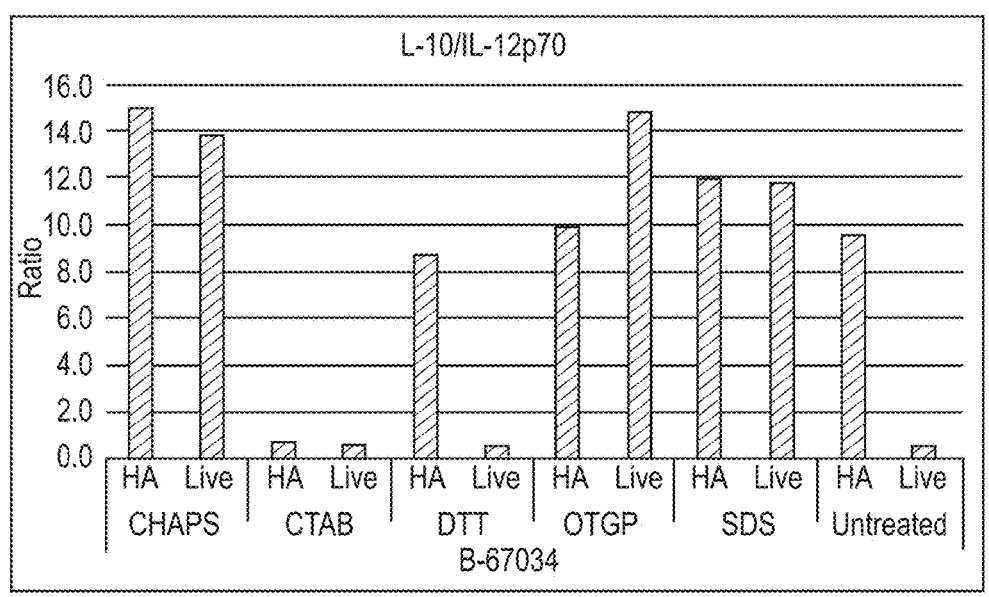
FIG. 3 depicts the ratio of IL-10/IL-12p70 for *M. luteus* NRRL B-67034 cells processed with 3-[(3-Cholamidopropyl)dimethylammoniol-1-propanesulfonate (CHAPS), Cetyl trimethylammonium bromide (CTAB), Dithiothreitol (DTT), Octyl-β-D-Thioglucpyranoside (OTGP), or Sodium Dodecyl Sulfate (SDS).

The PBMC assay as described in Example 1 was used to determine the ratio of IL-10/IL-12p70. The cytotoxic compounds CHAPS (4%, v/v), Octyl thioglucopyranoside (OTGP) (40 mM), and sodium dodecyl sulfate (SDS) (1% v/v) increased the IL-10/IL-12p70 ratio compared to untreated live cells (FIG. 3).

Example 3

Live Micrococcaceae cells were processed according to each of the following methods: (a) French Press; (b) autoclaving; (c) bead-beating; (d) chemical treatment and (e) heat treatment. For the French Press treatment, *M. luteus* NRRL B-67034 cells (30 mL, 100% stock as detailed above in Example 1) were run through the French Press (Thermo Spectronic; conditions: piston 1" Diameter; High ratio; PSI=1000 equivalent ~16,000 internal cell pressure). The flow-through was collected into a 50 mL conical tube on ice, and 5 mL of the flow through was transferred to a new tube. The remaining 25 mL was run through the French Press a second time, and the flow-through was collected in a 50 mL conical tube. The flow-through was aliquoted into 1 mL tubes and flash frozen and stored at −80° C. For autoclaving, the OD600 of *M. luteus* NRRL B-67034 cells in TSB culture (33° C. with shaking @ 200 rpm) was measured. The cells were washed 3× with Phosphate Buffered Saline (PBS, standard formula, no Ca or Mg) and were resuspended according to OD. Samples were placed in glass test tubes for autoclaving (20 min at 121° C./15 psi; Novus I by Getinge). For bead beating, 0.5 mL of each sample was transferred to the bead tube containing 0.1 mm silica/4 mm glass beads. Bead beating was done for 10-45 seconds (MPBio), and the entire volume removed to a fresh microcentrifuge tube. For the chemical treatment, 200 µL of cell suspension was pipetted into a 500 µL microcentrifuge tube and centrifuged at 16,000×g rcf for 1 min The supernatant was removed and discarded. For chemical treatment, CTAB (1% v/v) (200 µL) was pipetted into the tube containing cell residue. The tube was vortexed until the cells were fully resuspended. Following treatment, the tube was centrifuged to pellet the cells (12,000×g rcf for 1 minute), and the supernatant was discarded. To wash the cells, the cells were suspended in saline solution by vortexing and then centrifuged again to pellet the cells. The supernatant was discarded. The washing step was repeated twice more. For heat treatment, samples were placed into 50 mL conical tubes and heat processed for 30 min at 80° C. (water bath).

Figure 4A:
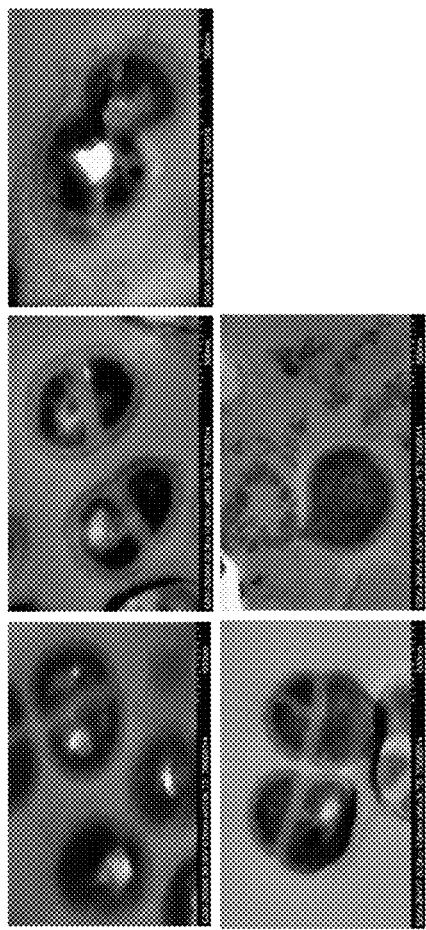
FIG. 4A depicts electron micrographs of cells that were heat-activated (HA) B-67033 (i), B-67034 (ii), 173C (iii), autoclaved B-67034 (iv), or processed with bead beating (BB) B67034 (v).
Figure 4B:
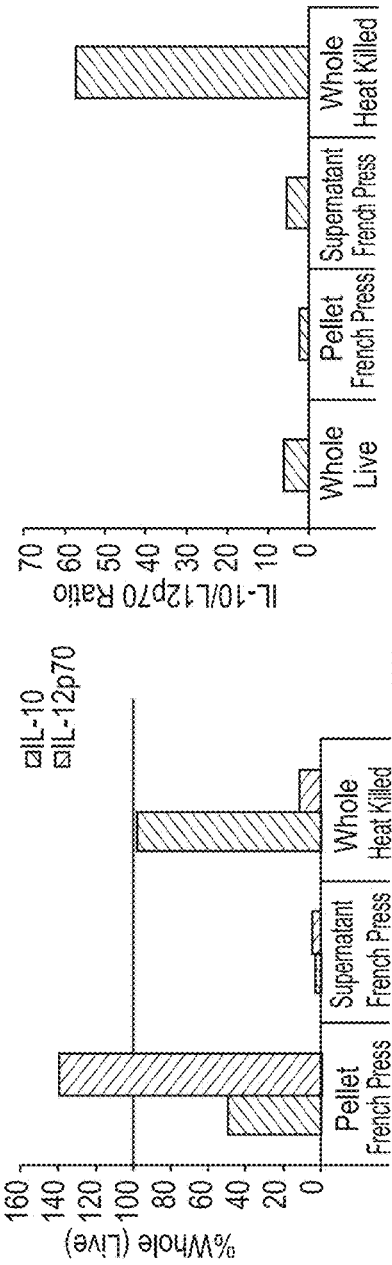
FIG. 4B depicts the effects of French Press treatment on IL-10, IL-12, and the ratio of IL-10/IL-12 compared to whole, heat-killed cells.
Figure 4C:
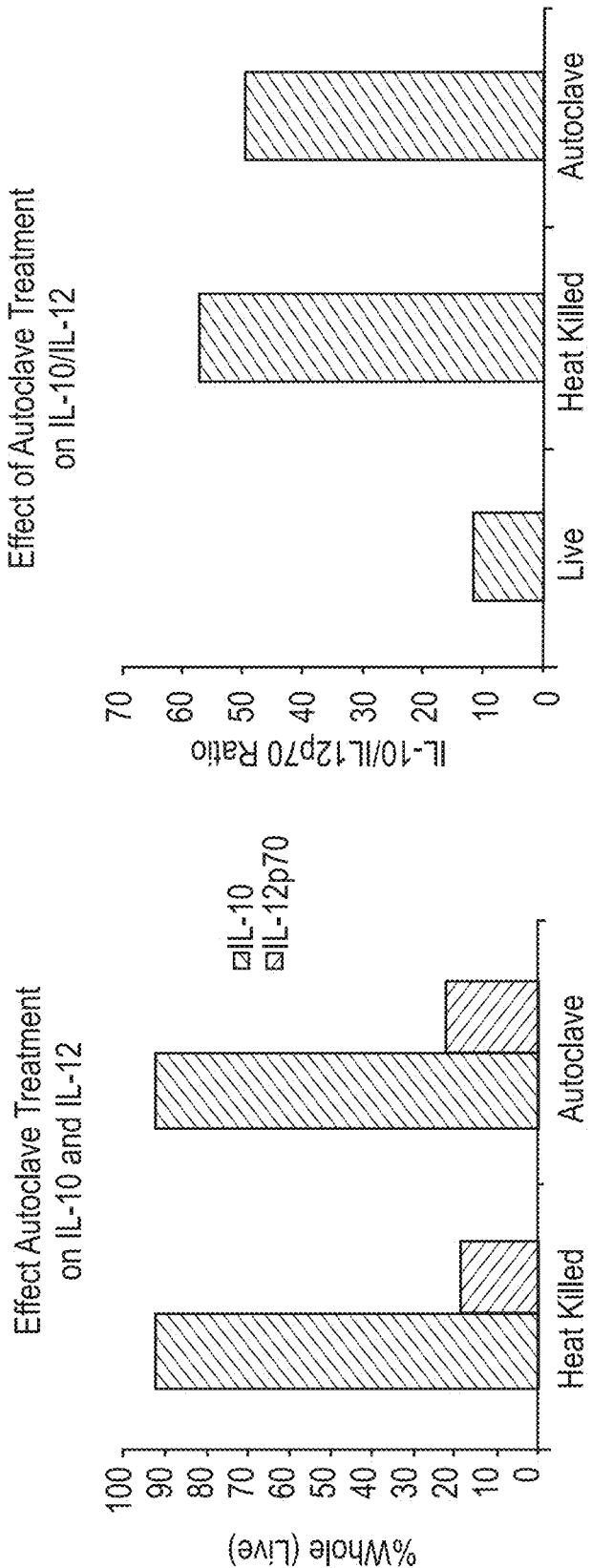
FIG. 4C depicts the effects of autoclave treatment on IL-10, IL-12, and the ratio of IL-10/IL-12, compared to whole, heat-killed cells.

Lysis of the cells and degradation of the cell wall was observed using electron microscopy when the cells were treated by bead beating (FIG. 4A-v) but not following heat processing (HA) (FIGS. 4A-i and 4A-ii, FIG. 4A-iv). FIG. 4A and the data in Table 1 demonstrate that the cell remains intact for preferred embodiments. The PBMC assay as described in Example 1 was used to determine the production of IL-10 and IL-12p70. Cells processed with the French Press exhibited a decreased IL-10/IL-12p70 ratio from incubation with PBMCs, compared to whole, heat-processed cells (FIGS. 4B and 4C), as did bead-beating (data not shown). As summarized in Table 1, heat processing, which resulted in whole, non-viable cells, increased the ratio of IL-10/IL-12p70 versus the IL-10/IL-12p70 ratio obtained from the *M. luteus* NRRL B-67034 live cells, measured using the PBMC assay, while treatments that lysed the cells reduced the ratio of IL-10/IL-12p70. These data indicated that lysing the cell is not a preferred embodiment; whereas methodologies that keep the cell whole, yet non-viable is preferred in that these methodologies have an increased ratio of IL-10/IL-12p70 (typically maintaining or slightly enhancing the IL10; while significantly decreasing the IL12).

TABLE 1

| *M. luteus* NRRL B-67034 | CTAB | Bead Beating | Heat Processed only |
|---|---|---|---|
| IL-10/IL-12 (Anti-inflammatory Capacity) | Reduced | Reduced | Increased |
| Evidence of Lysis | Yes | Yes | No |

Example 4

Tape strips were used to damage the skin on the forearms of human subjects. A composition comprising whole, non-viable *M. luteus* NRRL B-67034 cells at a concentration of 1.5% (v/v as compared with heat processed stock; see 100% description in example 1) or 7.5% (v/v as compared with heat processed stock, see 100% description in example 1) in PBS or the PBS vehicle alone were applied daily to the damaged area. Tape strips were used to collect samples for analysis of skin protein biomarkers IL-1Ra and IL-1α. Using clean tweezers, technicians apply a round D-Squame (Cuderm, D-100) tape on the designated sampling area. The sampling disc is pressed down on the site using the D-Squame disc applicator for 5 seconds, then released. The tape is gently removed with a clean tweezers and placed into a vial. Additional tapes are applied and removed in the manner listed above until 3 tapes per test site have been collected. Protein is extracted for cytokine analysis. The redness was measured using a Chroma Meter® (Minolta) and visual grading. The skin was visually graded for erythema/redness by a qualified human grader according to a scale of 0.0 (no redness) to 6.0 (extreme redness). A TEWL instrument (Aquaflux®; AF200 Biox Systems) was used to assess skin barrier damage and integrity.

Figure 5A:
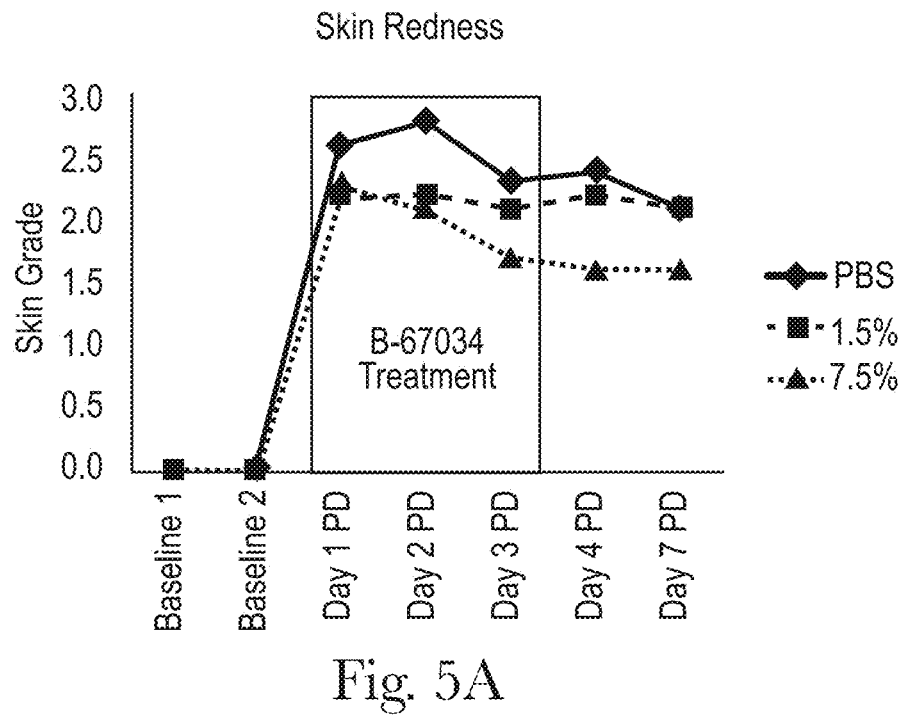
FIG. 5A depicts the skin redness grade (post tape strip damage (PD)) for skin treated with 1.5% (v/v; vs. 100% heat processed stock) or 7.5% (v/v; vs. 100% heat processed stock) whole, non-viable *M. luteus* NRRL B-67034 cells or PBS vehicle only.
Figure 5B:
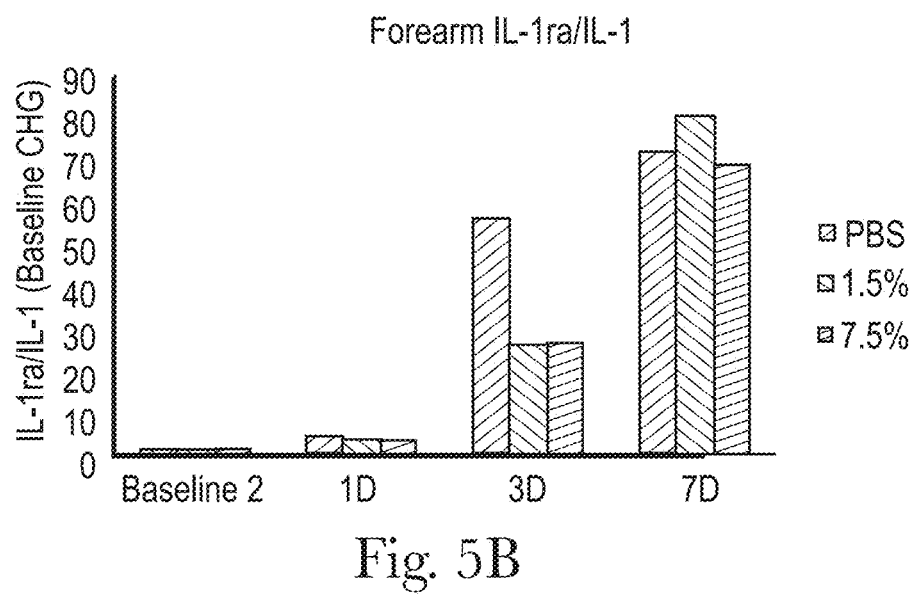
FIG. 5B depicts the ratio of IL-1Ra/IL-1α in skin protein samples from skin treated with 1.5% (v/v; vs. 100% heat processed stock) or 7.5% (v/v; vs. 100% heat processed stock) whole, non-viable *M. luteus* NRRL B-67034 cells or PBS vehicle only; after tape strip damage.

Skin processed with the PBS vehicle only exhibited greater skin redness than skin processed with the whole, non-viable bacteria. The 7.5% concentration of whole, non-viable *M. luteus* NRRL B-67034 cells resulted in the greatest decrease in skin redness after 7 days (FIG. 5A). After 3 days, the compositions comprising whole, non-viable *M. luteus* NRRL B-67034 cells resulted in a significant decrease in the IL-1Ra/IL-1α ratio compared to the PBS vehicle, indicating anti-inflammatory activity (FIG. 5B).

Example 5

The effects of a topical composition comprising processed Micrococcaceae cells according to the disclosure are assessed in a clinical study. Adult subjects are enrolled in an eight-week study. After a four-week washout period, the subjects are given a test product and a control product and apply each product twice daily to one-half of the face. The test product is a skin cream comprising processed *M. luteus* cells according to the disclosure in a dermatologically acceptable vehicle. The control product is the vehicle only.

Skin assessments are conducted at the start of the study (baseline) and after four and eight weeks of treatment. Skin barrier function is assessed used a Tewameter® TM300 (Courage+Khazaka Electronic GmbH) to measure transepidermal water loss. Skin hydration is measured with a Corneometer® (Courage+Khazaka Electronic GmbH). During the assessments, skin surface properties are measured with a high resolution camera (TiVi). Changes in redness, irritation, wrinkle volume, energy, variance, roughness, and smoothness are evaluated.

Additionally, the skin is analyzed for the presence of biomarkers of inflammation. Using clean tweezers, technicians apply a 25 mm, round D-Squame tape on the designated sampling area. The sampling disc is pressed down on the site using the D-Squame disc applicator for 5 seconds, then released. The tape is gently removed with a clean tweezers and placed into a 2 mL vial (Trace Analytical Core) with the tape side toward the inside of the tube. Additional tapes are applied and removed in the manner listed above until 3 tapes per test site have been collected. Biomarkers for inflammation are extracted in a buffered solution and analyzed by antibody-based detection.

The skin processed with the test product comprising processed *M. luteus* cells exhibits significant improvements in the signs of skin health compared to skin processed with vehicle only. The test product improves the barrier function of the skin, resulting in a significant decrease in TEWL. The test product also causes significant increases in skin hydration and smoothness, and significant decreases in skin redness, wrinkle volume, and overall roughness. The compositions and methods of the disclosure can comprise, consist essentially of, or consist of, the essential components, as well as optional ingredients described herein.

Example 6

Matrix Assisted Laser Desorption Ionization Time Of Flight (MALDI TOF) Mass Spectrometry was used for fast detection of a protein marker molecule released from cell samples of live *M luteus* NRRL B-67034 after sequential solvent extraction. Briefly, cells were extracted sequentially by water (Sample 1), 20% acetonitrile/water (Sample 2), 50% acetonitrile/water (Sample 3) and 80% acetonitrile/water (Sample 4) with pelleting by centrifugation in between. 5 µl of each solvent extract Sample was mixed with 5 µl of MALDI matrix α-cyano-4-hydroxycinnamic acid (CHCA at 10 mg/ml in 80% Acetonitrile/Water/0.1% trifluoracetic acid). 0.6 µl of this mixture was spotted on a MALDI target plate and allowed to air dry at room temperature before MALDI analysis. Water was chosen over PBS, as there was concern that upon concentration of the extract, the high concentration of salt may interfere with the PBMC assay as described in Example 1.

Figure 6:
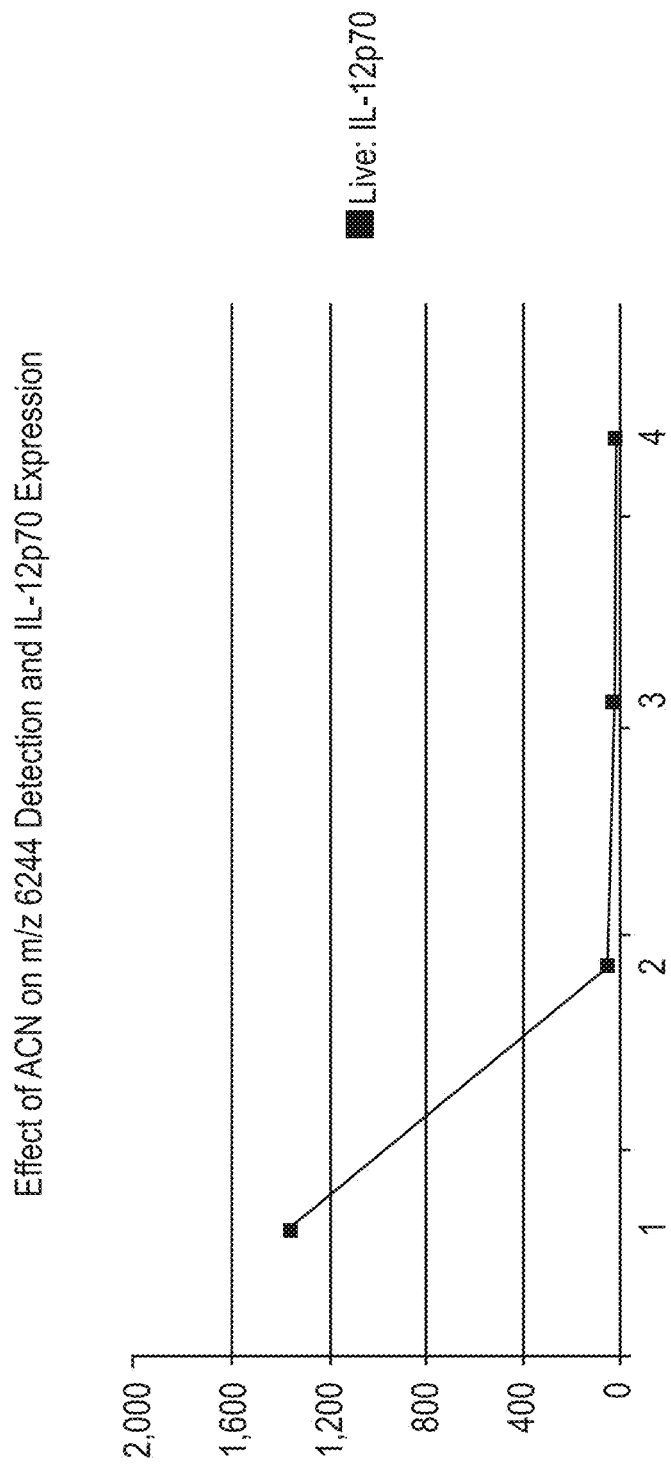
FIG. 6 depicts the level of m/z 6244 protein that is extracted from live *M. luteus* NRRL B-67034 cell following sequential solvent extraction (100% water, 20% acetonitrile/80% water, 50% acetonitrile/50% water and 80% acetonitrile/20% water) and detected by MALDI TOF mass spectrometry. On the same figure is also plotted the level of IL-12p70 induced in PBMCs treated with the same sequential solvent extractions solutions.

A MALDI TOF/TOF 4800 Plus Mass Analyzer (AB-Sciex, Framingham, Mass., USA) was used in the positive ion linear or reflectron mode. The mass spectrometer uses a 200-Hz frequency Nd:YAG laser, operating at a wavelength of 355 nm Ions generated by the MALDI ionization process were accelerated at 20 kV. FIG. 6 shows the intensity of the detected marker protein (m/z 6244, +/−5 Da) for the Samples 1, 2, 3 and 4 (Live: m/z 6244). The protein was initially detected in the *M. luteus* NRRL B-67034 extracts in the linear mode and confirmed the mass as m/z 6244 in the reflectron mode. The marker protein was sequenced using High Resolution Orbitrap LC-MS/MS. The cell surface associated marker protein, m/z 6244, extracts were dried and digested with enzyme trypsin at 37° C., overnight. The tryptic digest was then analyzed by online NanoLC (Waters, NanoAcquity, Milford, Mass.)-high resolution Orbitrap Elite mass spectrometry (Thermo Fisher, Schaumburg, Ill.). Mascot software (Matrix Science Corporation, London UK) identified the marker protein sequence as protein GIGDLNNLAN QHSDKINEAV DNAQEQHGDK LGEHGDTVNK GVDGAQEKFL SGDEGEQQA, (SEQ ID 1), with 100% sequence coverage. NCBI blast protein search of the sequence identified by mass spectrometry confirmed it as a *M. luteus* protein. The dissociated peptide sequence may also include a methionine at the beginning. It is known in the art the amino terminal methionine is enzymatically removed from the protein and thus may not be present in the excreted protein.

A BLAST search of this protein, and proteins of similar structure all appear associated with strains at the Family level as Micrococcaceae. Moreover, all of the *M. luteus* strains investigated have an open-reading frame (ORF) encoding for the m/z 6244 protein. Therefore, microbes suitable herein produce a protein with high sequence similarity scores to SEQ ID 1.

FIG. 6 also contains the IL12p70 PBMC data (using the assay as described in Example 1) for PBMC cells treated with samples 1, 2, 3 and 4 (Live: IL-12p70). FIG. 6 represents the challenges associated with using MALDI-TOF to detect the protein, and correlating to IL-12p70 expression in PBMCs. Acetonitrile (ACN) is a common solvent utilized for protein extraction and subsequent detection via mass spectrometry (MS). As ACN concentration increases, improving protein extraction from the cell surface and concomitant MS detection, levels of IL-12p70 expression induced in PBMCs treated with these samples diminishes to zero (likely due to disruption of protein tertiary or quaternary structure which would make it unrecognizable to PBMCs). However, sample 2 was extracted with enough ACN (20%) to detect the protein via MALDI-TOF and still permit quantitation of induction of IL-12p70 production in PBMC, via Meso Scale Discovery (MSD) ELISA. Sample 2 had an IL-12p70 level of 47.6 pg/ml, (*which was within the range for the MSD ELISA calibration curve) (FIG. 6). Co-detection of peak m/z 6244 in sample 2, and induction of IL-12p70 expression in PBMCs following treatment with sample 2, in conjunction with the drop in cell associated peak intensity of the protein between live and heat treated samples (as shown by loss of the protein of SEQ ID 1 to the supernatant of heat treated cells, FIG. 1C) suggests the protein corresponding to m/z 6244 induces IL-12p70 expression in PBMCs.

Preferred Micrococcaceae strains have a sequence identity of above 40% compared to SEQ ID 1. Highly preferred *Micrococcus luteus* strains have a sequence identity of above 95% compared to SEQ ID 1.

erence; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

```
                           SEQUENCE LISTING

<160> NUMBER OF SEQ ID NOS: 1

<210> SEQ ID NO 1
<211> LENGTH: 59
<212> TYPE: PRT
<213> ORGANISM: Micrococcus luteus

<400> SEQUENCE: 1

Gly Ile Gly Asp Leu Asn Asn Leu Ala Asn Gln His Ser Asp Lys Ile
1               5                   10                  15

Asn Glu Ala Val Asp Asn Ala Gln Glu Gln His Gly Asp Lys Leu Gly
            20                  25                  30

Glu His Gly Asp Thr Val Asn Lys Gly Val Asp Gly Ala Gln Glu Lys
        35                  40                  45

Phe Leu Ser Gly Asp Glu Gly Glu Gln Gln Ala
    50                  55
```

Example 7

The 80% acetonitrile/water extracts from live and heat activated Micrococcaceae cells were analyzed by Capillary Gel Permeation Chromatography (CapGPC)-Quadrupole Time-Of-Flight (QTOF) Mass Spectrometry (Waters Corporation, Milford, Mass.) with four 1 mm×15 cm TSK gel alpha 3000 columns in series (Tosoh Bioscience, Japan), 5 mM NH4Ac/water containing 10% acetonitrile, 25 μl/min flow rate isocratically. The data, acquired at high collision energy (CE=50V) over 60 minutes, indicated the presence of polysaccharide fragment marker ions, a possible marker of anti-inflammatory activity.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" All numeric ranges are inclusive of narrower ranges; delineated upper and lower range limits are interchangeable to create further ranges not explicitly delineated. All measurements made are at 25° C. unless otherwise designated. All statistical analyses are performed such that a p-value of less than or equal to 0.05 indicates statistical significance.

All documents cited in the Detailed Description of the Invention are, in relevant part, incorporated herein by ref-

What is claimed is:

1. A method of increasing anti-inflammatory activity of a population of *Micrococcus luteus* cells comprising processing the cells to produce whole, non-viable cells, wherein processing the cells comprises irradiating the bacteria with gamma or ultraviolet radiation, wherein the processed cells increase the ratio of IL-10/IL-12 produced by peripheral blood mononuclear cells in vitro.

2. The method of claim 1, wherein the processed cells decrease the production of interleukin-12 by peripheral blood mononuclear cells in vitro, compared to living or lysed Micrococcaceae cells.

3. The method of claim 1, wherein the processed cells maintain or increase the production of interleukin-10 by peripheral blood mononuclear cells in vitro, compared to living or lysed Micrococcaceae cells.

4. The method of claim 1 wherein the processed cells have liberated a cell associated proinflammatory inducing protein with greater than 40% sequence identity scores to SEQ ID 1.

5. A method of increasing anti-inflammatory activity of a population of *Micrococcus luteus* comprising processing the cells to produce whole, non-viable cells, wherein processing the cells comprises heating the cells at a temperature between about 60° C. and about 150° C., wherein the processed cells increase the ratio of IL-10/IL-12 produced by peripheral blood mononuclear cells in vitro.

6. The method of claim 5, wherein processing the cells comprises heating the cells for about 30 seconds to about 40 minutes.

7. A method of increasing anti-inflammatory activity of a population of *Micrococcus luteus* cells comprising processing the cells to produce whole, non-viable cells, wherein processing the cells comprises contacting the cells with a compound selected from the group consisting of a chaotrope, a detergent, an acidic solution, and combinations thereof, wherein the processed cells increase the ratio of IL-10/IL-12 produced by peripheral blood mononuclear cells in vitro.

8. The method of claim 5, wherein the processed cells decrease the production of interleukin-12 by peripheral blood mononuclear cells in vitro, compared to living or lysed Micrococcaceae cells.

9. The method of claim 5, wherein the processed cells maintain or increase the production of interleukin-10 by peripheral blood mononuclear cells in vitro, compared to living or lysed Micrococcaceae cells.

10. The method of claim 5 wherein the processed cells have liberated a cell associated proinflammatory inducing protein with greater than 40% sequence identity scores to SEQ ID 1.

11. The method of claim 7, wherein the processed cells decrease the production of interleukin-12 by peripheral blood mononuclear cells in vitro, compared to living or lysed Micrococcaceae cells.

12. The method of claim 7, wherein the processed cells maintain or increase the production of interleukin-10 by peripheral blood mononuclear cells in vitro, compared to living or lysed Micrococcaceae cells.

13. The method of claim 7 wherein the processed cells have liberated a cell associated proinflammatory inducing protein with greater than 40% sequence identity scores to SEQ ID 1.

* * * * *